United States Patent
Van Hal et al.

(10) Patent No.: US 7,253,325 B2
(45) Date of Patent: Aug. 7, 2007

(54) PROCESS FOR THE PREPARATION OF ALKYLENE GLYCOLS

(75) Inventors: Jaap W. Van Hal, Fresno, TX (US); John S. Ledford, Richmond, TX (US); Xiankuan Zhang, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 11/541,764

(22) Filed: Oct. 2, 2006

(65) Prior Publication Data

US 2007/0066856 A1 Mar. 22, 2007

Related U.S. Application Data

(62) Division of application No. 10/955,796, filed on Sep. 30, 2004, now Pat. No. 7,161,046.

(51) Int. Cl.
*C07C 29/00* (2006.01)
*C07C 31/00* (2006.01)
*C07C 31/02* (2006.01)
*C07C 33/00* (2006.01)

(52) U.S. Cl. .................................................... 568/840

(58) Field of Classification Search ..................... None
See application file for complete search history.

(56) References Cited

OTHER PUBLICATIONS

Schaus et al (Journal of the American Chemical Society, (2002), 124(7), 1307-1315.*

* cited by examiner

*Primary Examiner*—Thurman K. Page
*Assistant Examiner*—Kellette Gale
(74) *Attorney, Agent, or Firm*—Jim Wheelington

(57) ABSTRACT

Disclosed is a process for the preparation of alkylene glycols from the corresponding alkylene oxide, such as ethylene glycol from ethylene oxide, in the presence of water, a catalyst and, optionally, carbon dioxide. The catalyst is a SALEN-type compound which contains an amino group and an oxy or hydroxy group connected by a hydrocarbon, such as an alkyl or an alkylaryl. The SALEN-type compounds may be Schiff bases, i.e., a condensate product of a primary amine with an aldehyde, ketone or an alcohol.

The SALEN-type compound may be a mono or bis compound and may be complexed with a Group 4-14 metal, such as aluminum, tin, vanadium, chromium, manganese, iron, cobalt or platinum.

13 Claims, 8 Drawing Sheets

PROCESS FOR THE PREPARATION OF ALKYLENE GLYCOLS

This is a divisional application of application Ser. No. 10/955,796 filed Sep. 30, 2004 now U.S. Pat. No. 7,161,046.

BACKGROUND OF THE INVENTION

1. Field of the Invention

This invention relates to a process for the preparation of alkylene glycols from the corresponding alkylene oxide in the presence of water and a SALEN-type catalyst. A specific example of the process is in the preparation of ethylene glycol from ethylene oxide.

2. Description of the Prior Art

The production of alkylene glycols from alkylene oxides is known and is practiced commercially. Of particular interest is the production of ethylene glycol from ethylene oxide. The thermal hydration of ethylene oxide in water produces monoethylene glycol (MEG), a major active component in antifreeze. MEG can also be used as a base material in the production of polyester fibers, resins, films and bottles.

Hydration of ethylene oxide can be through catalytic and non-catalytic means. Non-catalytic hydration of ethylene oxide to MEG requires a large excess of water to inhibit the formation of diethylene glycol (DEG) and other higher glycols. Even with a large excess of water the molar selectivity to MEG is only about 90%. In addition, the water must be distilled from the glycol to obtain a high purity product.

Catalytic hydration of ethylene oxide may use smaller amounts of water and is carried out at lower temperatures. There are numerous examples of catalysts for hydration of an alkylene oxide to alkylene glycol.

N,N'-bis(salicylidene)ethylenediamino(SALEN)-type compounds are known. A metal may be associated with the SALEN-type compound to form a metallosalenate.

U.S. Pat. No. 5,665,890 discloses a process for producing a stereoselectively or regioselectively enriched product by reacting a nucleophile and a chiral or prochiral cyclic substrate in the presence of a non-racemic chiral catalyst. Examples of nucleophiles are amines, mercaptans and alcohols. Epoxides, aziridines, episulfides and certain other cyclic compounds are examples of the substrate. The catalyst may be a metallosalenate catalyst. One reaction disclosed is the asymmetric ring-opening of symmetrical epoxides to resolve a racemic mixture. Hydrolytic kinetic resolution of racemic mixtures having terminal epoxide groups is disclosed in U.S. Pat. No. 6,448,414.

U.S. Pat. No. 5,902,835 discloses a method of preparing polyurethane foam by reacting an organic polyisocyanate with a polyol in the presence of water and a combination of a gelling catalyst and a blowing catalyst. The blowing catalyst may be titanium isopropoxy-SALEN.

U.S. Pat. No. 6,440,745 discloses a method for the combinatorial synthesis, screening and characterization of supported and unsupported organometallic compounds as catalysts, additives and therapeutic agents. SALEN compounds were included as a base scaffold to prepare ligand libraries.

SUMMARY OF THE INVENTION

This invention is a process for the preparation of alkylene glycols from an alkylene oxide and water in the presence of a SALEN-type compounds of general formulae $R_1$—$NR_2O$ or $R_{3-7}Ar$—$NR_2OH$ where $R_1$ is an alkyl of 1 to 6 carbon atoms, $R_2$ is hydrogen or an alkyl, aryl, cycloalkyl, alkylamino group of two to six carbon atoms, halogens, an alkenyl of two to six carbon atoms, hydroxyl, nitro, thiol, amines, amino, imines, amide, phosphoryls, phosphonates, phosphines, carbonyls, $R_{3-7}$ are substituents on aromatic ring Ar and are hydrogen, an alkyl or cycloalkyl group and may be the same or different (see FIGS. 1 and 2). These SALEN compounds may be mono or bis compounds or may be complexed with a Group 4-14 metal, such as aluminum, tin, vanadium, chromium, manganese, iron, cobalt or platinum.

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE INVENTION

Figure 1:
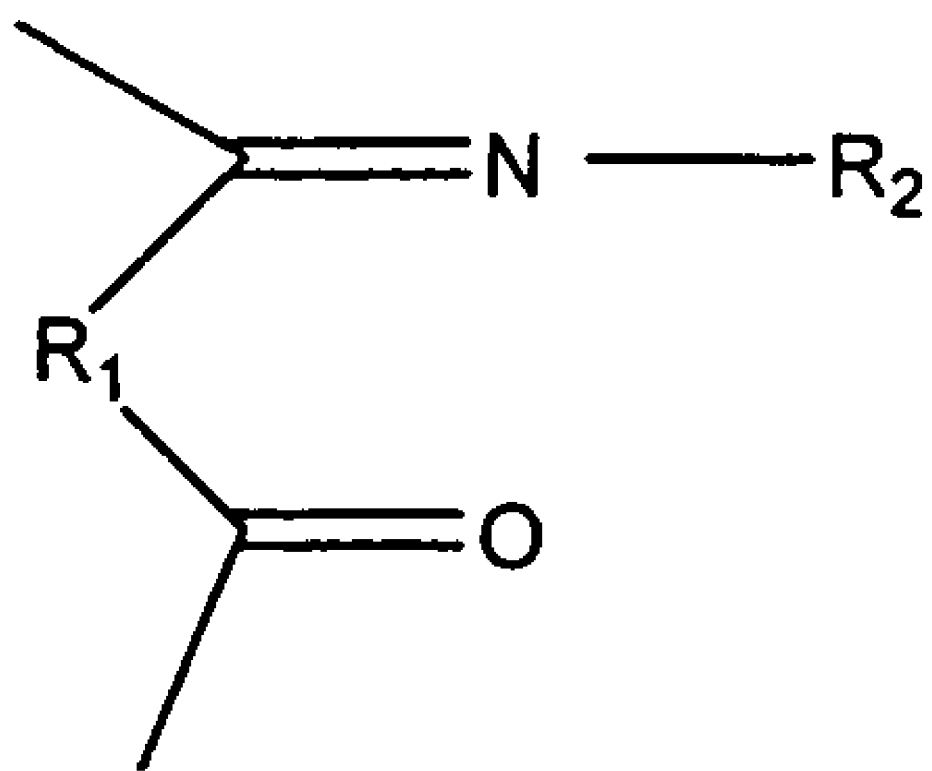
FIG. 1 is a structural representation of alkyl SALEN-type compounds.

Alkylene glycols can be obtained by reacting the corresponding alkylene oxide with water. A catalyst may be added to improve activity of the reaction and the selectivity to the glycol.

Alkylene oxides are generally of the formula $R^1R^2(COC)R^3R^4$, where each $R^1$, $R^2$, $R^3$ and $R^4$ is independently hydrogen, an alkyl of from 1 to 4 carbon atoms or an aryl of from 6 to 10 carbon atoms.

Examples of alkylene oxides are ethylene oxide, propylene oxide and butylene oxide. The corresponding alkylene glycol is generally of the formula $R^1R^2(COHCOH)R^3R^4$, where $R^1$, $R^2$, $R^3$ and $R^4$ are as defined above, and may be obtained by hydration of the alkylene oxide, i.e., reacting it with water to introduce a hydroxyl group and hydrogenate the oxygen. A mixture of glycols is formed (monoalkylene glycol, dialkylene glycol and higher alkylene glycols).

Though the reaction of alkylene oxide and water to alkylene glycol proceeds non-catalytically, improvements in reaction rate, selectivity and reduced water can be realized by the use of catalysts. The catalysts used in the present invention are SALEN-type or metallosalenate compounds.

As noted above, SALEN-type and metallosalenate compounds have been used to kinetically resolve chiral epoxides by selectively hydrating one enantiomer over another with a chiral, nonracemic catalyst, such as salenates and metallos alenates (U.S. Pat. No. 6,448,414, Example 18 in which racemic mixtures of compounds having a terminal epoxide are contacted with SALEN-Co(III)benzoate to produce enantioenriched (unreacted) epoxides and (reaction product) diols.

The present invention is not concerned with reacting a racemic mixture of epoxides for kinetic resolution to a particular isomer by converting the other isomers to diols. In the present invention, conversion of all epoxides, such as ethylene oxide, to diols, such as ethylene glycols, is preferable and the selective conversion to a particular diol, such as monoethylene glycol, is more preferable.

The term "racemic" means a mixture of dextrorotatory and levorotatory isomers which is not optically active. The term "chiral" describes a molecule which is not capable of being superimposed on its mirror image. One example of chirality is a carbon atom which is bonded to four different elements or radicals. The term "enantiomer" means a chiral isomer, i.e., a non-racemic molecule which is not capable of being superimposed on its mirror image.

SALEN-type compounds or metallosalenate compounds of the present invention may be chiral but it is not necessary or desirable that they are non-racemic. SALEN-type compounds of the present invention contain an amino group and an oxy or hydroxy group which are connected by a hydrocarbon, such as an alkyl or an alkylaryl, may be mono or bis compounds and may be ligands coordinated with a metal. The SALEN-type compounds of the present invention may be Schiff bases, i.e., a condensate product of a primary amine with an aldehyde, ketone or an alcohol.

Figure 3:
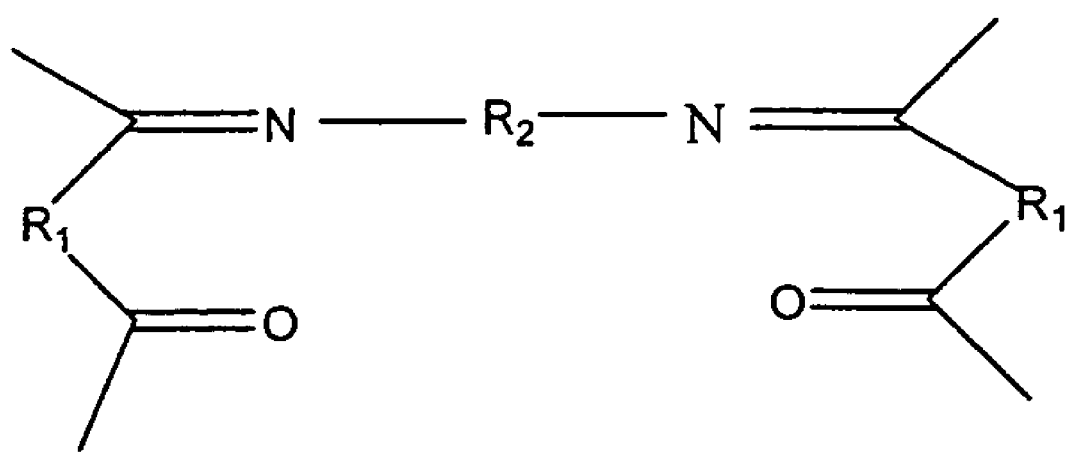
FIG. 3 is a structural representation of N,N'-bisacetylacetone-alkylene diamino SALEN-type compounds.
Figure 5:
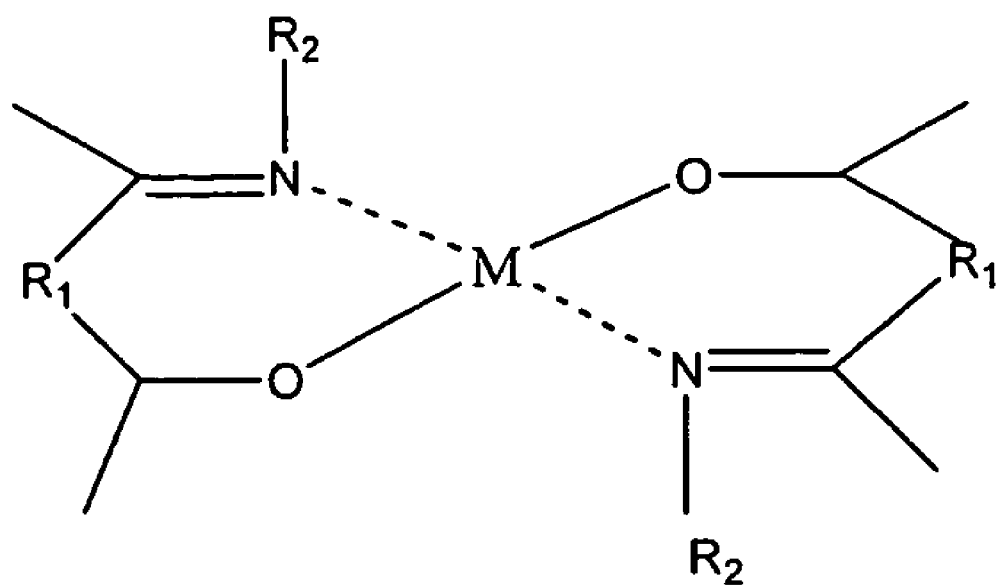
FIG. 5 is a structural representation of bis[acetylacetonatealkylamino] SALEN-type metallosalenate compounds.
Figure 6:
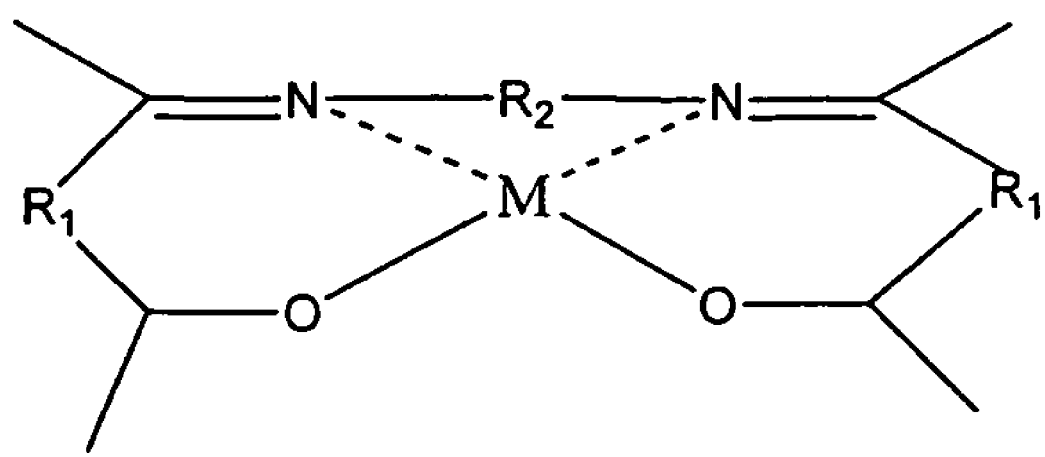
FIG. 6 is a structural representation of N,N'-bis(acetylacetone-alkylene diamino) SALEN-type metallosalenate compounds.

One class of SALEN-type compounds of the present invention is of the general formula $R_1$—$NR_{20}$ where $R_1$ is an alkyl of 1 to 6 carbon atoms and $R_2$ is hydrogen or an alkyl, aryl, cycloalkyl, alkylamino group of two to six carbon atoms, halogens, an alkenyl of two to six carbon atoms, hydroxyl, nitro, thiol, amines, amino, imines, amide, phosphoryls, phosphonates, phosphines or carbonyls. This type of SALEN compound may be mono of the general formula $R_1$—$NR_{20}$ where $R_1$ and $R_2$ are as described above (FIG. 1), bis of the general formula $(R_1$—$NO)_2R_2$ where $R_1$ and $R_2$ are as described above (FIG. 3) or a metal complex of the general formula $M(R_1$—$NO_2R_2)_2$ (FIG. 5) or of the general formula $M(R_1$—$NO_2)_2R_2$ (FIG. 6) where $R_1$ and $R_2$ are as described above and M is a metal of Group 4-14, such as aluminum, tin, vanadium, chromium, manganese, iron, cobalt or platinum, preferably cobalt, more preferably cobalt (III). The metals may have an oxidation state of (II) or (III). If the metal has an oxidation state of (III), the metallosalenate exists as a (+1) cation with a (−1) anion, such as acetate ($CH_3COO$), boron tetrafluoride ($BF_4$), boron tetra pentafluorophenyl ($B(C_6F_5)_4$), or triflate ($CF_3SO_3$).

Another class of SALEN-type compounds of the present invention is of the general formula $R_{3-7}Ar$—$NR_2OH$ where $R_{3-7}$ is hydrogen, an alkyl or cycloalkyl group and Ar is an aromatic ring.

Figure 2:
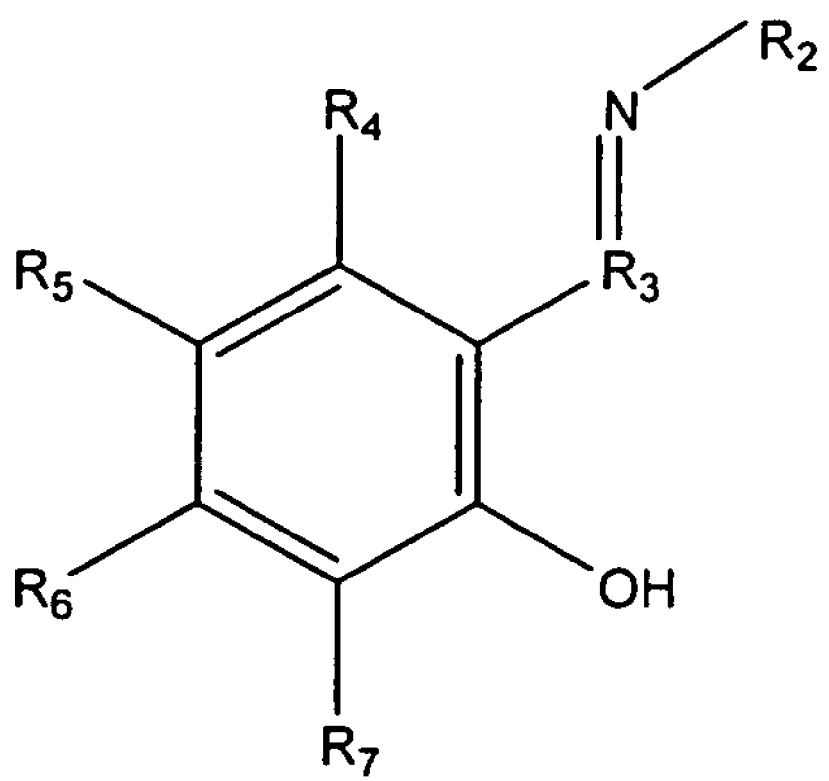
FIG. 2 is a structural representation of alkylaryl SALEN-type compounds.
Figure 4:
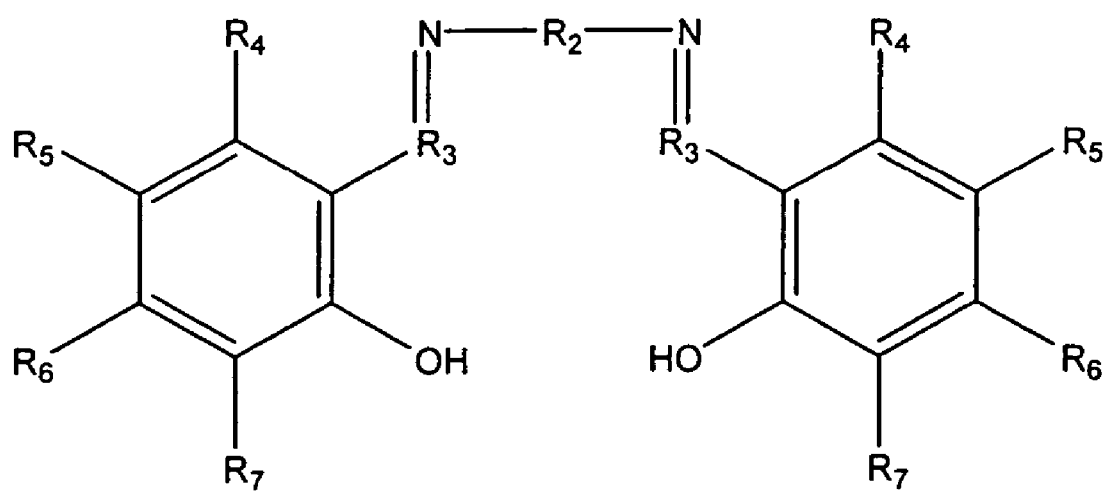
FIG. 4 is a structural representation of N,N'-bis(salicylidene)alkylenediamino SALEN-type compounds.
Figure 7:
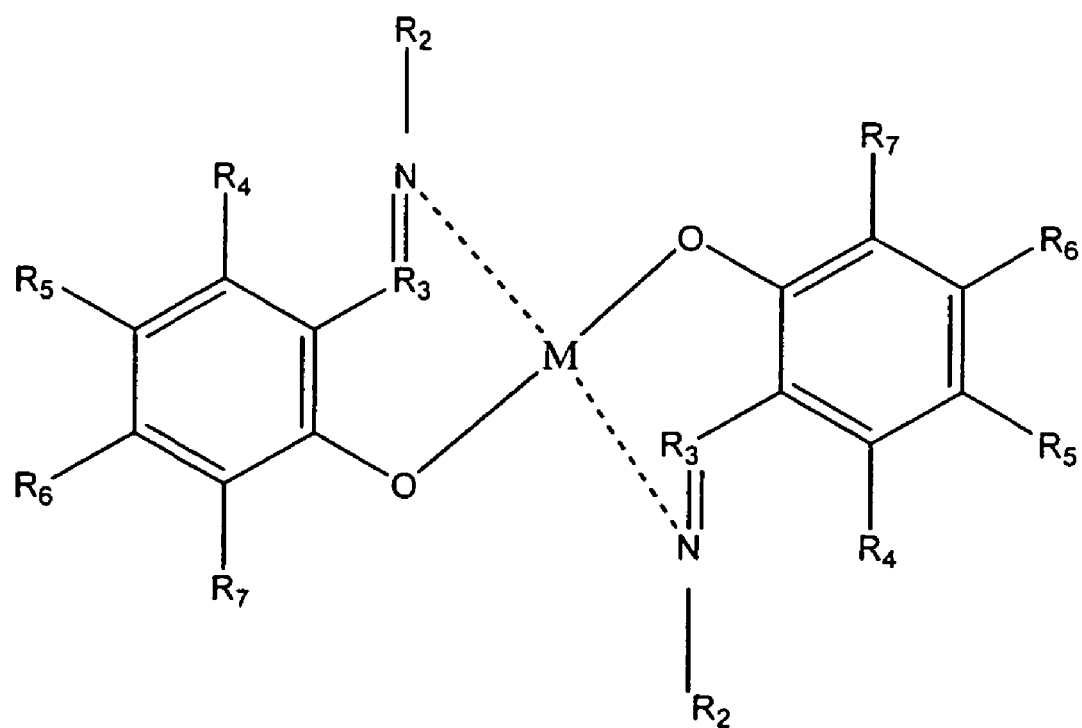
FIG. 7 is a structural representation of bis[salicylidenealkylamino] SALEN-type metallosalenate
Figure 8:
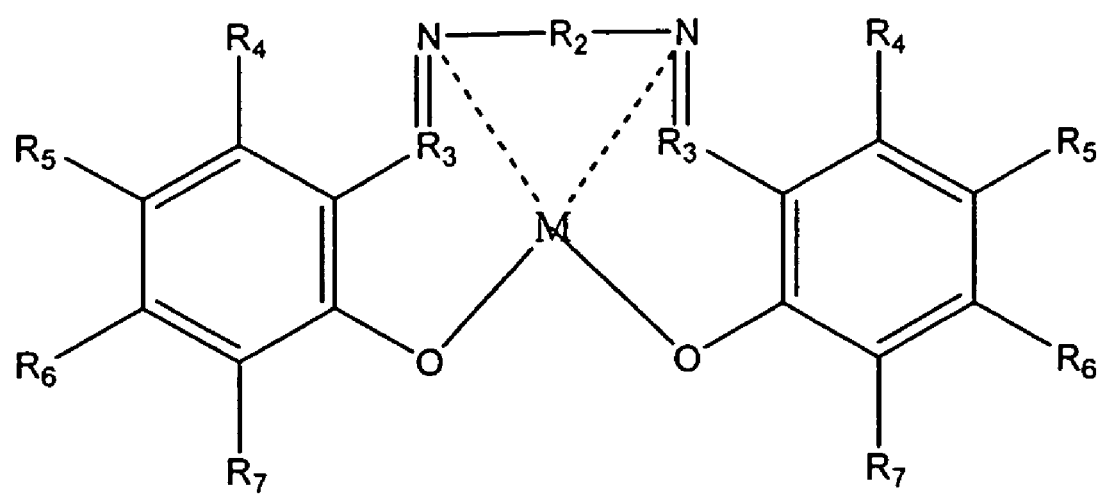
FIG. 8 is a structural representation of N,N'-bis(salicylidene)alkylenediamino SALEN-type metallosalenate compounds.

This type of SALEN compound may be mono of the general formula $R_{3-7}Ar$—$NR_2OH$ where $R_{3-7}$ and Ar are as described above (FIG. 2), bis of the general formula $(R_{3-7}Ar$—$NOH)R_2$ where $R_2$, $R_{3-7}$ and Ar are as described above (FIG. 4) or a metal complex of the general formula $M(R_{3-7}Ar$—$NR_2OH)_2$ (FIG. 7) or of the general formula $M(R_{3-7}Ar$—$NOH)R_2$ (FIG. 8) where $R_2$, $R_{3-7}$, Ar and M are as described above. Examples of the substituents on the aromatic ring are $R_3$ and $R_5$ being t-butyl.

Methods of making SALEN-type and metallosalenate compounds are known in art. Examples of preparation of such compounds are disclosed in U.S. Pat. No. 6,448,414, hereby incorporated by reference.

The catalysts used in the present invention may be heterogenized using procedures known in the art, examples found at J. Am. Chem. Soc., 1999, vol. 121, p. 4147-4154; Inorg. Chem., 2004, vol. 43, p. 2967-2974; J. Catal., 2004, vol. 225, p. 398-407; J. Mol. Catal. A., 2004, vol. 218, p. 141-146 and PCT WO 03059512. The catalysts may be supported on resins, zeolite, clay, alumina, silica or carbon.

In a process for preparing an alkylene glycol by reacting alkylene oxide with water in the presence of a catalyst of the present invention, a mixture of alkylene oxide and water in the liquid state is contacted with a SALEN-type catalyst. The process is carried out at a temperature from about 20° C. to 250° C., preferably 50° C. to 200° C. and a pressure greater than atmospheric, preferably 25 psig to 1000 psig with the temperature and pressure selected to maintain liquid phase conditions. The molar ratio of water to alkylene oxide is in the range from about 5 to 25.

The invention having been generally described, the following examples are given as particular embodiments of the invention and to demonstrate the practice and advantages thereof. It is understood that the examples are given by way of illustration and are not intended to limit the specification or the claims to follow in any manner.

The following compounds were purchased from commercially available sources (Aldrich):
N,N'-bis(salicylidene)ethylenediamine
N,N'-bis(salicylidene)-1,3-propanediamine
N,N'-bis(salicylidene)-1,4-butanediamine
N,N'-bis(salicylidene)-1,6-hexanediamine
N,N'-bis(salicylidene)-1,2-phenylenediamine
(R,R)-(−)-N,N'-bis(3,5-di-tert-butylsalicylidene)-1,2-cyclohexanediamine or (S,S)-(+)-N,N'-bis(3,5-di-tert-butylsalicylidene)-1,2-cyclohexanediamine The following compounds were prepared similar to the literature method described for N,N'-bis(salicylidene)ethylenediamine in "Synthetic Methods of Organometallic and Inorganic Chemistry", Vol 1, p. 81, Ed by W. A. Herrmann, by Herrmann and Zybill, or J. Am. Chem. Soc., 1955, 77, 5820 from the aldehyde or ketone and amine:
bisacetylacetone-ethylenediamine
N-salicylidene-aniline These compounds were evaluated as catalysts for the catalytic hydration of ethylene oxide to ethylene glycol. All experiments were performed in a batch mode in a Multiclave™. EO and water mixture was dosed into the individual tubes of the Multiclave™ at reaction temperature using a stream selector valve, a pump and a timer. Products were analyzed by GC using a FID detector. Selectivities to MEG, DEG and TEG are calculated using the number of moles of EO used to form the glycols. Reactions were run for 10 hours at 100° C. or for 72 hours at room temperature. Listed below are the results of the experiments. Selectivities were compared to a control experiment using a tube filled with the same volume but with no catalyst present (Comparative Example).

EXAMPLE 1

N,N'-bis(salicylidene)ethylenediamine

Approximately 0.6 g of SALEN ligand dissolved in 1 ml water was loaded into each reactor tube of the Multiclave™, and 5 ml of 4:1 (weight ratio) water/EO was added at 100° C. The reactor was blanketed with 250 psig of $N_2$. The experiment with the same SALEN ligand dissolved in 5 ml of water and treated with carbon dioxide over the weekend at room temperature was repeated but with 250 psig of $CO_2$ as blanket gas.

The results are listed in Table 1.

EXAMPLE 2

N,N'-bis(salicylidene)-1,3-propanediamine

The procedure for Example 1 was repeated. The results are listed in Table 1.

EXAMPLE 3

N,N'-bis(salicylidene)-1,4-butanediamine

The procedure for Example 1 was repeated. The results are listed in Table 1.

EXAMPLE 4

N,N'-bis(salicylidene)-1,6-hexanediamine

The procedure for Example 1 was repeated. The results are listed in Table 1.

EXAMPLE 5

N,N'-bis(salicylidene)-1,2-phenylenediamine

The procedure for Example 1 was repeated. The results are listed in Table 1.

EXAMPLE 6 bisacetylacetone-ethylenediamine

The procedure for Example 1 was repeated. The results are listed in Table 1.

EXAMPLE 7

N-salicylidene-aniline

The procedure for Example 1 was repeated. The results are listed in Table 1.

TABLE 1

Selectivity to MEG on SALEN ligands in the absence or presence of $CO_2$

| EXAMPLE | MEG selectivity with $N_2$ | MEG selectivity with $CO_2$ |
|---|---|---|
| Comparative | 83% | 88% |
| 1 | 52% | 93% |
| 2 | 62% | 93% |
| 3 | 48% | 92% |
| 4 | 66% | 91% |
| 5 | 82% | 89% |
| 6 | 79% | 91% |
| 7 | 79% | 90% |

The following compound was purchased from commercially available sources (Aldrich):
Cobalt-N,N'-bis(salicylidene)-1,3-propanediamine The following compounds were prepared from Co(II) acetate and a stoichiometric amount of SALEN ligand in boiling methanol:
Cobalt(II)-N,N'-bis(salicylidene)ethylenediamino
Cobalt(II)-bis(N-salicylidene-aniline)
Cobalt(II)-N,N'-bis(salicylidene)-1,6-hexanediamine

EXAMPLE 8

Cobalt(II)-N,N'-bis(salicylidene)ethylenediamino

Approximately 0.3 g of Co(II) SALEN compound dissolved in 5 ml water was loaded into each reactor tube of the Multiclave™, and 5 ml of 4:1 (weight ratio) water/EO was added at 100° C. The reactor was blanketed with 250 psig of either $N_2$ or $CO_2$. The results are listed in Table 2.

EXAMPLE 9

Cobalt(II)-bis(N-salicylidene-aniline)

The procedure for Example 1 was repeated. The results are listed in Table 2.

EXAMPLE 10

Cobalt(II)-N,N'-bis(salicylidene)-1,3-propanediamine

The procedure for Example 1 was repeated. The results are listed in Table 2.

EXAMPLE 11

Cobalt(II)-N,N'-bis(salicylidene)-1,6-hexanediamine

The procedure for Example 1 was repeated. The results are listed in Table 2.

TABLE 2

Selectivity to MEG using Cobalt(II)SALEN in the presence of $N_2$ or $CO_2$

| EXAMPLE | MEG selectivity with $N_2$ | MEG selectivity with $CO_2$ |
|---|---|---|
| Comparative | 87% | 89% |
| 8 | 82% | 86% |
| 9 | 86% | 88% |
| 10 | 73% | 91% |
| 11 | 87% | 88% |

EXAMPLE 12

N,N'-bis(salicylidene)ethylenediamine

Approximately 1 mmol of SALEN ligand dissolved in acetic acid solution was loaded into each reactor tube of the Multiclave™, and 5 ml of 4:1 (weight ratio) water/EO was added at 100° C. The results are shown in Table 3.

EXAMPLE 13

N,N'-bis(salicylidene)-1,3-propanediamine

The procedure for Example 1 was repeated. The results are listed in Table 3.

TABLE 3

Selectivity to MEG using SALEN ligands in the presence of Acetic Acid.

| EXAMPLE | Acetic acid added | MEG selectivity |
|---|---|---|
| Comparative 1 | None | 88% |
| Comparative 2 | 0.05 M to 1 M | 89% |
| 12 | None | 66% |
| 12 | 1 mmol | 74% |
| 12 | 2 mmol | 93% |
| 12 | 3 mmol | 94% |
| 12 | 4 mmol | 95% |
| 12 | 5 mmol | 95% |
| 13 | 2 mmol | 90% |
| 13 | 4 mmol | 93% |

Cobalt(III)-(R,R)-(−)-N,N'-bis(3,5-di-tert-butylsalicylidene)-1,2-cyclohexanediamine acetate or Cobalt(III)-(S,S)-(+)-N,N'-bis(3,5-di-tert-butylsalicylidene)-1,2-cyclohexanediamine acetate was prepared from the commercially available cobalt (II) compounds (Aldrich) in toluene in the presence of acetic acid and air as described in J. Am. Chem. Soc., 2002, 124, 1307 (Jacobsen and co-workers).

EXAMPLE 14

Cobalt(III)-(R,R)-(−)-N,N'-bis(3,5-di-tert-butylsalicylidene)-1,2-cyclohexanediamine acetate or Cobalt-(S,S)-(+)-N,N'-bis(3,5-di-tert-butylsalicylidene)-1,2-cyclohexanediamine acetate The solid was dissolved in 5 mL of di-glyme. The reactor was blanketed with $N_2$ and 5 mL of 4:1 EO/water was dosed in each tube. The reaction was run for 72 hours at room temperature. The EO conversion was close to complete at the end of the run. The results are shown in Table 4.

TABLE 4

Selectivity to MEG using R and S compounds at room temperature

| Metal Compound | Amount | MEG selectivity |
|---|---|---|
| 14-R | 0.07 g. | 97% |
| 14-R | 0.13 g. | 98% |
| 14-R | 0.21 g. | 98% |
| 14-S | 0.08 g. | 97% |
| 14-S | 0.15 g. | 98% |
| 14-S | 0.20 g. | 98% |

The above data demonstrates that SALEN-type compounds containing —$NR_1OH$ or —$NR_2O$ where $R_1$ is an alkyl of 2 to 6 carbon atoms and $R_2$ is an alkylaryl of 7 to 10 carbons atoms are effective for the catalytic hydration of ethylene oxide to ethylene glycol (Table 1). The presence of carbon dioxide improves the selectivity to monoethylene glycol when compared to thermal hydration (Tables 1 and 2). The addition of acetic acid also improves the selectivity to monoethylene glycol when compared to thermal hydration (Table 3). Other acids which should have the same effect are any acid that forms a weakly coordinating counterion, such as benzoic acid, triflic acid and sulphonic acid. Cobalt (II) metallosalenate compounds are effective for the catalytic hydration of ethylene oxide to ethylene glycol (Table 2). Cobalt (III) metallosalenate compounds show improved selectivity to monoethylene glycol when compared to thermal hydration (Table 4).

Obviously, numerous modifications and variations of the present invention are possible in light of the above teachings. It is therefore to be understood that within the scope of the appended claims, the invention may be practiced otherwise than as specifically described herein.

The invention claimed is:

1. A process for the preparation of alkylene glycols comprising reacting an alkylene oxide with water in the presence of a compound selected from the group consisting of

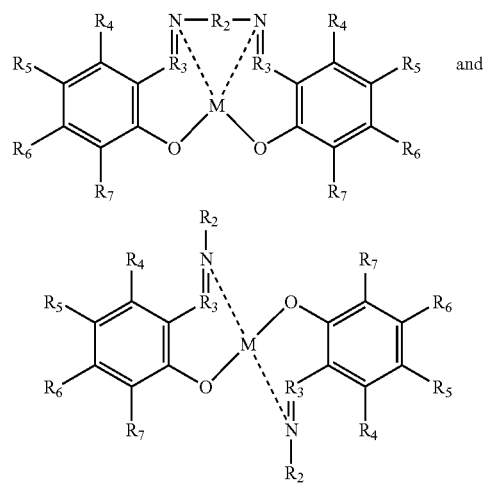

wherein R3 is an alkyl or cycloalkyl and wherein R4-7 are hydrogen, alkyl or cycloalkyl and may be same or different, R2 is, alkyl or aryl or cycloalkyl or alkylamino of two to six carbon atoms, halogen, alkenyl of two to six carbon atoms, hydroxyl, nitro, thiol, amine, amino, imine, amide, phosphoryl, phosphonate, phosphine or carbonyl and R2 may be also be hydrogen in structure II and M is a metal of Group 4-14, wherein the process is carried out at a molar ratio of water to alkylene oxide in the range from about 5 to 25, and wherein the compound is not non-racemic.

2. The process as in claim 1 wherein M is aluminum, tin, vanadium, chromium, manganese, iron, cobalt or platinum.

3. The process as in claim 2 wherein M is cobalt.

4. The process as in claim 3 wherein the metal is in a valence state of 2.

5. The process as in claim 1 wherein $R_3$ and $R_5$ are t-butyl.

6. The process as in claim 1 wherein the compound is Cobalt(III)-N,N'-bis(salicylidene)-1,6-hexanediamine, Cobalt(III)-N,N'-bis(salicylidene) ethylenediamino, Cobalt (II)-bis(N-salicylidene-aniline), Cobalt(III)-N,N'-bis(salicylidene)-1,3-propanediamine, Cobalt(III)-(R,R)-(−)-N,N'-bis(3,5-di-tert-butylsalicylidene)-1,2-cyclohexanediamine or Cobalt(III)-(S,S)-(+)-N,N'-bis(3,5-di-tert-butylsalicylidene)-1,2-cyclohexanediamine.

7. The process as in claim 1 wherein the process is carried out at a temperature from about 20° C. to 250° C.

8. The process as in claim 7 wherein the temperature is 50° C. to 200° C.

9. The process as in claim 1 wherein the process is carried out at a pressure greater than atmospheric.

10. The process as in claim 9 wherein the pressure is 25 psig to 1000 psig.

11. The process as in claim 1 wherein the alkylene oxide is reacted with water in the presence of carbon dioxide or nitrogen.

12. The process as in claim 1 wherein the alkylene oxide is reacted with water in the presence of any acid that forms a weakly coordinating counterion.

13. The process as in claim 12 wherein the acid is acetic acid, benzoic acid, triflic acid or sulphonic acid.

* * * * *